United States Patent [19]
Ledard et al.

[11] Patent Number: 5,141,561
[45] Date of Patent: Aug. 25, 1992

[54] BONY OR DENTAL FILLING BIOMATERIALS AND PROCESSES FOR PREPARATION THEREOF

[75] Inventors: Claude Ledard, Nantes; Edmond Benque; Jean-Louis Lacout, both of Toulouse; Christian Rey, Castanet Tolosan, all of France

[73] Assignee: Whereas, Agence Conseil 3P, Levallois Perret, France

[21] Appl. No.: 594,124

[22] Filed: Oct. 9, 1990

[30] Foreign Application Priority Data

Oct. 9, 1989 [FR] France ................ 89 13246

[51] Int. Cl.$^5$ .............................................. C09K 3/00
[52] U.S. Cl. .......................................... 106/35; 501/1; 423/308; 423/311; 106/161; 433/228.1
[58] Field of Search ............... 106/35, 161; 423/308, 423/311; 501/1

[56] References Cited

U.S. PATENT DOCUMENTS

| | | | |
|---|---|---|---|
| 4,861,733 | 8/1989 | White | 501/1 |
| 4,904,257 | 2/1990 | Mori et al. | 623/16 |
| 4,917,702 | 4/1990 | Scheicher et al. | 623/16 |
| 5,009,898 | 4/1991 | Sakuma et al. | 424/618 |

OTHER PUBLICATIONS

Giourdon, Jean Claude et al.; "EPR of a Synthetic Oxidized Apatite", *C. R. Acad. Sci.* Ser B 276(13) 559–62.

Montrejaud, et al., "Sur l'Aystitude du Réseau Apatitique A. Fixer des Molécules d'Oxygéne", *Colloq. Int. C.N.R.S.,* 230 (Phys. Chem. Christallogr. Apatites Interet Biol.) 481–6.

Primary Examiner—William R. Dixon, Jr.
Assistant Examiner—Margaret Einsmann
Attorney, Agent, or Firm—Harold H. Dutton, Jr.

[57] ABSTRACT

The invention relates to a biomaterial for bony or dental fillings on the basis of apatite. It provides a biomaterial having antiseptic properties for limiting the proliferation of microorganisms at the site of implantation. The biomaterial according to the invention is based on calcium oxygenated phosphate having an apatitic structure which has oxygenated species with degrees of oxidation greater than or equal to $-2$. This biomaterial brings together with the antiseptic properties mentioned above an excellent biocompatibility, a very low solutility and good qualities of osteo-induction.

21 Claims, No Drawings

BONY OR DENTAL FILLING BIOMATERIALS AND PROCESSES FOR PREPARATION THEREOF

The invention relates to a bone or tooth filling biomaterial. It provides a filling able to favor a rehabilitation by bone or tooth tissue and permits a partial or complete substitution of the biomaterial by the tissue. The invention relates also to processes for the production of said biomaterial.

BACKGROUND AND OBJECTS OF THE INVENTION

Biomaterials based on calcium phosphate, and in particular based on hydroxyapatite $Ca_{10}(PO_4)_6(OH)_2$, are known for intraosteo or intradental filling. One can refer, for example, to the following publications concerning these apatitic biomaterials: "Jarche M. Kay J.F., Gumaer KI, Doremus R.H and Drobeck H.P Tissue, cellular and subcellular events at a bone-ceramic hydroxylapatite interface. J. Bioeng 1, 79, 1977"; "Ducheyne P and de Groot K, In vivo surface activity of a hydroxyapatite alveolar bone substitute, J. Biomed. Mater. Res. 14, 225, 1980"; "Klaas de Groot, Bioceramics of calcium phosphate, C.R.S. Press Inc., New York, 1983".

These biomaterials are known to have the following properties:

excellent biocompatibility (very limited risk of inflammatory rejection reactions), very low solubility (low tendency to disappear in the medium over a course of several months after implantation), osteoinduction quality (tendency to favor the reconstruction of bones).

These properties which make this material very appropriate for the production of bone or dental fillings, come from their chemical composition and their crystallographic structure, which are close to those of the mineral part of calcified tissue.

However, these known apatitic biomaterials are inactive with respect to pathogenic microorganisms susceptible of developing in the tissues. Thus, these biomaterials have essentially a mechanical role (bone filling and substitution) and have no antiseptic property: they are totally incapable of limiting the development of bacteria, funguses . . . which are present before intervention (caries, periodontal illnesses, . . . ) or which are the result thereof (aseptic imperfections, especially in the mouth, inflammations . . . ).

The present invention seeks to provide a new biomaterial having, as do the aforementioned known materials, an apatitic structure which confers excellent qualities of biocompatibility and osteoconduction or induction, but which has antiseptic properties making it capable of limiting the proliferation of microorganisms at the site of implantation.

The invention thus seeks to protect the graft in a local manner at the site of the implantation, while avoiding a use of antibiotics in general. It also seeks to assure this protection in a continuous manner over time, throughout the entire duration in which the material remains present at the implantation site.

Another object of the invention is to permit, after the case treated, adapting the scope of action of the biomaterial to the character of the microorganisms present or likely to develop at the site of implantation (in particular in order to fight in a specific manner against anaerobic microorganisms).

DESCRIPTION OF THE INVENTION

To this end, the bone or dental filling biomaterial according to the invention comprises oxygenated calcium phosphate (ApO) having an apatitic structure containing oxygenated species with degrees of oxidation greater than or equal to $-2$, of the formula:

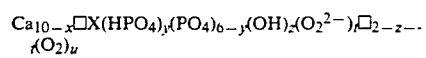

$$Ca_{10-x}\square_x(HPO_4)_y(PO_4)_{6-y}(OH)_t(O_2^{2-})_z\square_{2-z-u}(O_2)_u$$

wherein $\square$ represents a lacuna or vacancy, $0 \leq x \leq 1$ $0 \leq y \leq 1$ $0 \leq t \leq 1$ $0 \leq u \leq 1$ $u + t \geq 0.2$ and $z = 2 + y - x - 2t$.

Such a biomaterial contains in the channels of its apatitic structure at least one of the two following species: $O_2^{2-}$, $O_2$. Experiments have shown that these species were liberated in the medium either by progressive dissolution of the material, or by chemical exchange with the medium. The specie $O_2^{2-}$ (peroxide ion) thus liberated acts in situ to destroy the microorganisms with a well known effectiveness for this specie; the specie $O_2$ (molecular oxygen) acts in a specific manner on anaerobic microorganisms while locally increasing the partial pressure of oxygen. While retaining the apatitic structure and the desirable properties of biocompatibility and osteoconduction or induction, the biomaterial according to the invention thus produces an effect of protection of the implantation site with respect to any appearance or development of pathogenic organisms. The speed of dissolution in the medium, and thus the effective period of duration of the material may be adjusted by causing the stoichiometry of the apatitic structure to vary, and particularly the coefficients x and y, the number of vacancies at the calcium site and the number of $HPO_4$ ions being directly connected to the speed of dissolution (material slightly soluble for $x < 0.1$, $y < 0.1$ and increasing solubility for $x > 0.1$, $y > 0.1$).

The invention provides in particular three sub-families of the previously defined biomaterial.

The biomaterial of the first sub-family contains, at the same time, the species $O_2^{2-}$ and $O_2$ in such a manner as to present an antiseptic action on microorganisms in general (the presence of $O_2^{2-}$), reinforced with respect to anaerobic microorganisms (the presence of $O_2$). The biomaterial of this sub-family comprises an oxygenated calcium phosphate (ApO) having an apatitic structure in which the coefficients are such that:

$0.1 \leq x \leq 0.4$ y is slightly different from x $t \leq u/2$ $0.2 \leq u \leq 0.8$.

It should be noted that the solubility of this biomaterial may be adjusted over a large range from a low solubility ($x$ on the order of 0.1) to a high solubility ($x$ on the order of 0.4).

The biomaterial of the second sub-family contains essentially the species $O_2^{2-}$ and simply traces of the species $O_2$. This material very rich in the peroxide group has generally a very effective antiseptic action. The biomaterial of this subfamily comprises an oxygenated calcium phosphate (ApO) having an apatitic structure in which the coefficients are such that:

$$0.2 \leq x \leq 0.5$$

$y$ slightly different from $x$ $$0.8 \leq t \leq 1$$

$$u \leq 0.1.$$

This material (coming as will be seen below from a low temperature production) has a coefficient $x$ greater than 0.2 (a relatively high number of vacancies) and thus a solubility generally more significant than the previous material.

The biomaterial of the third sub-family contains exclusively the species $O_2$ such that it presents a selective action which is very effective vis-a-vis anaerobic microorganisms. This biomaterial is important in practice because they are generally micro-organisms of this type which develop in the implantation medium. Further, in certain cases, it is preferable to avoid the general destructive action of the species $O_2^{2-}$, in particular to preserve certain micro-organisms which develop a favorable action. The biomaterial of this third sub-family comprises an oxygenated calcium phosphate (ApO) of the following apatitic structure:

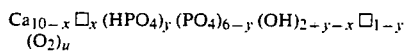

wherein
$0 \leq x \leq 0.2$
$0 \leq y \leq 0.2$
$0.2 \leq u \leq 0.8.$

The solubility of this biomaterial is generally lower than that of the previous ones, but may be adjusted to a precisely satisfactory value to assure a sufficient local pressure of oxygen. It should be noted that, generally, the presence of pathogenic microorganisms causes a local reduction of the pH which increases the dissolution of the biomaterial and therefor the liberation of oxygen at the time of need.

The biomaterial of the invention may be used, especially in the case in which the active species $O_2^{2-}$ and $O_2$ are of low percentage ($t$ and $u$ are low) or when located at a site with a high risk of inflammation (intervention on a carie or bone disease such as osteomyelitis). It may also be used mixed with other materials in a known combination in order to associate the appropriate qualities of these materials to these biomaterial antiseptic ones according to the invention. The additives may in particular be the following: non-oxygenated apatitic calcium phosphate, designated as hydroxyapatite HAp of the formula $Ca_{10}(PO_4)_6(OH)_2$ (characteristics: very low solubility, good mechanical strength and high porosity giving good qualities of osteoconduction); tricalcium phosphate PTCa of the formula $Ca_3(PO_4)_2$ (generally of low strength by reason of its high solubility); calcium carbonate $CaCO_3$ (natural or synthetic) and or calcium sulfate $CaSO_4$ (low cost and taken with expansion); blood coagulation derivatives, in particular fibrin, fibrinogen . . . ; collagen (maleability and adherence) eventually completed with glycoaminoglycanes and chondroitine sulfate (osteoinductive activity).

Further, it is possible to partially substitute carbonate ions ($CO_3$) for the hydrogenophosphate ions ($HPO_4$) in the oxygenated apatitic structure according to the invention. This substitution comes closer to the composition of the biomaterial of the mineral part of the bone, while retaining the antiseptic character of the biomaterial.

The invention also relates to processes for production of the biomaterial according to the invention permitting production of oxygenated apatite appropriate to each application, processes permitting in particular the production of biomaterials according to the three sub-families defined above.

It will be noted that oxygenated apatite has already been obtained in the laboratory by Dale R. Simpson in 1969 ("D. R. Simpson, oxygen rich apatite, The Am. Min., Vol. 54, p. 560–562, March–April 69"). D. Simpson has shown that this compound was soluble in hydrochloric acid and liberated oxygen capable of oxidizing a copper electrode with heating. However, this punctual laboratory production does not permit adjusting the coefficients of the various species and obtaining the desired substance.

According to a first manner of preparation according to the invention, the process comprises placing in suspension a calcium phosphate from the following group: tricalcium phosphate (PTCa), dicalcium phosphate (DCPD), or octocalcium phosphate (OCP), in an aqueous solution containing oxygenated water, for a period of time as a function of the coefficients $x$, $y$, $t$ and $u$ desired, physically separating the solid phase and the liquid phase and drying the solid phase.

According to another mode of preparation, the process comprises reversing into an aqueous solution containing oxygenated water, a soluble calcium salt and ammonium phosphate, at a pH, and a temperature, and for a period of time as a function of the coefficients $x$, $y$, $t$ and $u$ desired, allowing the ripening of the precipitate obtained in the mother solution, physically separating the solid phase and the liquid phase and drying the solid phase.

The second mode of preparation will preferably be chosen for favoring the strength of the peroxide ions of the biomaterial.

To optimize this preparation, and avoid the formation of foreign phases and loss of reactants, the quantities of calcium salts and ammonium phosphate returned into the aqueous solution of oxygenated water are such that the atomic ratio Ca/P is between 1.4 and 2.

In the two methods of preparation, the pH at the time of growth or precipitation is preferably fixed at a value between 5 and 9, such that the higher is the value, the lower are the desired coefficients $x$ and $y$ in the ranges $0 \leq x \leq 1$ and $0 \leq y \leq 1$. Preferably the pH is adjusted by the addition of ammonium, the ammonium ion being only slightly troublesome and easily eliminated.

The temperature during the evolution or the precipitation is advantageously fixed at a value comprising between 20° C. and 100° C., such that the higher are the values of the temperature, the lower are the desired coefficients x, y and t in the ranges $0 \leq x \leq 1$, $0 \leq y \leq 1$, $0 \leq t \leq 1$.

The period during which the suspension is allowed to evolve, or during which is carried out the precipitation is an important factor for obtaining at the same time a good crystallization of the apatite and the desired values of the coefficients x, y and t.

This period is advantageously fixed at a value between 2 minutes and 300 hours, the longer the time, the lower are the desired coefficients within the ranges $0 \leq x \leq 1$, $0 \leq y \leq 1$, $0 \leq t \leq 1$.

In the case of preparation by precipitation, the pouring of the calcium and phosphorous salts is carried out progressively in the solution of oxygenated water for the period mentioned above. For long durations, this pouring is done dropwise with an appropriate flow.

The concentration in oxygenated water of the aqueous solution acts on the concentrations of $O_2^{-2}$ and of $O_2$. Preferably, an aqueous solution of oxygenated water of a concentration between 5 and 50 volumes is selected, the higher the desired concentration, the higher are the coefficients t and u in the ranges $0 \leq t \leq 1$, $0 \leq u \leq 1$.

Regardless of the manner of carrying out, the process of preparation may be completed by a supplementary calcination step of the solid phase at a temperature less than 450° C., the higher is the desired temperature T, the lower is the coefficient in the range $0 \leq t \leq 1$.

This calcination modifies the composition of the biomaterial while transforming the peroxide species $O_2^{-2}$ into molecular oxygen $O_2$. The calcination thus reduces the coefficient t at the expense of the coefficient u, but nonetheless an overall loss of oxygen is observed, the sum $t+u$ obtained being less than the initial sum $t+u$. Moreover, this calcination improves the state of crystallization and reduces the solubility of the product. As it is carried out at average temperatures, the final solubility of the calcined biomaterial remains sufficient to confer on it good antiseptic properties at the implantation site.

To obtain a biomaterial comprising an association of oxygenated apatite and one or more of the supplementary materials from the above mentioned group, it is sufficient to mix by physical means and in a homogeneous manner the dry solid phase of ApO obtained with the one or more compounds desired in the form of a finely divided solid or in the form of an aqueous gel: HAp, PTCa, $CaCO_3$, $CaSO_4$, collagen, glycoaminoglycane, chondroitine sulfate.

In the case of an aqueous gel of collagen, the mixture may be lyophilized in order to obtain a dry powder ready to be used.

To prepare the biomaterial already defined in which the hydrogenophosphate ions are substituted by the carbonate ions, potassium or sodium carbonate is added to the solution containing the oxygenated water, and the process is then carried out as indicated above. In practice, this addition remains very low with respect to the quantity of other components (the $CO_3/Ca$ atomic ratio $\leq 0.05$) in order to obtain a very minor substitution.

DESCRIPTION OF PREFERRED EMBODIMENTS

The description which follows provides examples of the preparation of biomaterials according to the invention and test results.

The methods of analysis used are in any case conventional methods of solid chemistry:

X-ray diffraction: the diffraction of X-rays permits establishing the crystallographic structure while carrying out the counting, the classification and the determination of the positions of the rays. A more powerful examination permits also to define the crystalline parameters of the matrix, and to give an idea (width of the lines) of the crystalline state. Finally, the diffraction of the X-rays permits assuring, depending on the sensitivity of the method, the purity of the compound.

Infrared adsorption spectrometry: infrared adsorption spectrometry permits establishing the bonds between the atomic groups. In the case of apatites, determinations can in particular be made of:

hydroxyl ions: bands at 3560 and 740 $cm^{-1}$, carbonate ions bands 1420 $cm^{-1}$, phosphate bands and more particularly the band due to $HPO_4^=$, Phosphorous determination: the determination of phosphorous (orthophosphate ions) is carried out by chemical analysis by a colorimetric method: formation of an orange phosphomolybdic complex. By this method, the total of orthophosphate ions is determined (in our case $PO_4^{3-}$ and $HPO_4^=$), determination of $HPO_4^=$ ions: the determination of only the $HPO_4^=$ ions is carried out by analysis before and after calcination at 1000° C. The dosage before calcination permits dosing the total of the $PO_4^{3-}$ and $HPO_4^=$ ions. The calcination transforms the $HPO_4^=$ ions into $P_2O_7^{4-}$ ions. The difference between the dosage before and after calcination permits obtaining the corresponding value of only the $HPO_4^=$ ions, determination of molecular oxygen: the determination of molecular oxygen is carried out by measuring the volume displaced during the acid dissolution; in the presence of carbonate, one must first absorb the $CO_2$ liberated on sodium asbestos, determination of peroxide ions $O_2^=$: after acidic dissolution (1N perchloric acid) the peroxide ions $O_2^=$ are titrated by manganimetry.

EXAMPLE 1

Preparation of Biomaterial

A solution of 1 liter of water oxygenated to 30 volumes by dilution of a commercial solution at 110 volumes is prepared, and in this solution is dissolved 2.6 grams of diammonium hydrogenphosphate $(NH_4)_2HPO_4$ (solution 1). A solution of 100 milliliters of water containing 7.08 grams of calcium nitrate $(Ca(NO_3)_2.6H_2O$ (solution 2) is prepared. Solution 1 is brought to a temperature of 90° C., and the pH is adjusted to 8.5 by the addition of the necessary quantity of ammonia solution. Solution 2 is poured into solution 1 all at once; it is allowed to stand one hour at 90° C. while maintaining the pH at the value of 8.5. The precipitate is separated from the mother solution by filtration on a buchner filter, and the recovered solid is dried.

All of the reactants are of pharmaceutical grade. This preparation permits preparing about 3.5 grams of biomaterial.

The biomaterial is an apatite of the formula:

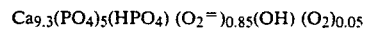

$Ca_{9.3}(PO_4)_5(HPO_4)(O_2^=)_{0.85}(OH)(O_2)_{0.05}$

EXAMPLE OF PREPARATION NO. 2

A solution of 1 liter of oxygenated water to 30 volumes of a commercial solution is prepared by dilution to 110 volumes and the pH is adjusted to a value of 8.5 by addition of a sufficient quantity of dilute ammonia solution (to the tenth). 50 grams of finely divided β-tricalcium phosphate ($Ca_3(PO_4)_2$) are added to this solution. This suspension is agitated slowly by means of a magnetic stirrer and heated to reflux for 10 hours at a temperature near the boiling point. A pH measuring electrode, supporting the temperature (Metrohm type) permits controlling the pH permanently: in case of variation, it is brought back to the control value of 8.5 by the addition of ammonia solution diluted one tenth. The suspension is then allowed to cool. The solid is separated from the solution by filtration in a buchner funnel and is washed with 2 liters of distilled water for eliminating all salts in solution. The solid is dried in air in an oven at 30° C. for 5 hours, then is heated in air for one hour at 430° C. About 45 grams of a pulverulent solid are obtained; it is characterized by X-ray diffraction, infrared absorption spectrometry, and chemical analysis. It is represented by the following formula:

$$Ca_{9.9}(PO_4)_{5.9}(HPO_4)_{0.1}(OH)(O_2)_{0.5}$$

EXAMPLE 3

Preparation of a Canalary Filling Paste

A first very simple preparation was produced. It comprises carefully mixing: 0.5 gram of oxygenated apatite prepared according to Example 1, with 0.5 gram of hydroxyapatite stoichiometrically, and 0.1 gram of anhydrous calcium sulfate ($CaSO_4$). Each of the different constituents is first pulverized (about 5 microns); the mixture is also carefully homogenized. It may be kept in a hermetically sealed flask. At the time of using the mixture it is made into a paste and brought to the desired consistency by the addition of distilled water (about 1 ml per 50 mg). This paste may then be used for closing the canalary by means of the professional instruments conventionally used for this purpose.

EXAMPLE 4 FOR PREPARATION OF A PASTE

The preparation is analogous to that previously described. One simply replaces the added distilled water by the addition of a solution to 0.5% of native veal collagen.

EXAMPLE 5 FOR PREPARATION OF GRANULES

According to the method of preparation of Example 2 one can also prepare granules. For this, after washing and filtering the solid is recovered, dried in an oven at 80° C. until it is brought to a consistency enabling granulation (the percentage of water is about 10%). It is then granulated in a machine of the "FREWITT MG 6A" type. The upper limit is fixed at 400 microns and the lower at 200 microns. The granules are then calcined in air for one hour at 430° C.

EXAMPLE 6

Results of in Vitro Tests

The effectiveness of the biomaterials according to the invention, based on oxygenated apatite, has been tested in vitro on anaerobic bacteria. Two roots have been kept:

*bacteroides fragilis* (from the collection of the Pasteur Institute, NCTC 9343),

*fusobacterium nucleatum* (from the collection of the Pasteur Institute Ref. 6039).

These two strains were selected because they are strictly anaerobic and because they are found in different human pathologies.

The principle of these in vitro tests consists in placing together the anaerobic bacteria different concentrations of apatite in broth suspension under controlled conditions of anaerobiosis and determining the number of these bacteria after 48 hours and 72 hours of contact. The result is constituted by apatite containing no oxygenated species.

Observed in the two cases were a significant reduction by a factor of 1000 of the number of anaerobic bacteria.

EXAMPLE 7

In Vivo Implantation

Several tests have been carried out in vivo on dogs both on canalary obturation and in periodontal filling. The implants behave in a manner analogous to implants produced from other hydroxyapatites. No sign of rejection or inflammation was noted.

We claim:

1. A biomaterial for bony or dental filling, having antiseptic properties for limiting the proliferation of microorganisms at the site of implantation, characterized in that it comprises oxygenated calcium phosphate (ApO) having an apatitic structure having oxygenated species with degrees of oxidation greater than or equal to $-2$, of the formula:

$$Ca_{10-x}\square_x(HPO_4)_y(PO_4)_{6-y}(OH)_t(O_2^{2-})_z\square_{2-z-u}(O_2)_u$$

where $\square$ represents a vacancy $0 \leq x \leq 1$ $0 \leq y \leq 1$ $0 \leq t \leq 1$ $0 \leq u \leq 1$ $u + t \geq 0.2$ and $z = 2 + y - x - 2t$.

2. A biomaterial as in claim 1, characterized in that it comprises an oxygenated calcium phosphate (ApO) with an apatitic structure in which the coefficients are such that:

$0.1 \leq x \leq 0.4$ y is slightly different than x $t \leq u/2$ $0.2 \leq u \leq 0.8$.

3. A biomaterial as in claim 1, characterized in that it comprises an oxygenated calcium phosphate (ApO) having an apatitic structure in which the coefficients are such that:

$0.2 \leq x \leq 0.5$ y is slightly different than x $0.8 \leq t \leq 1$ $u < 0.1$.

4. A biomaterial characterized in that it comprises an oxygenated calcium phosphate (ApO) of the following apatitic structure:

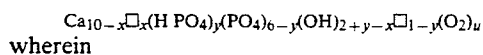

wherein
$0 \leq x \leq 0.2$
$0 \leq y \leq 0.2$
$0.2 \leq u \leq 0.8$.

5. A biomaterial as in claim 1, characterized in that it comprises a mixture of oxygenated apatitic calcium phosphate (ApO) of the aforesaid formula and a non-oxygenated apatitic calcium phosphate (HAp) of the formula $Ca_{10}(PO_4)_6(OH)_2$.

6. A biomaterial as in claim 1, characterized in that it comprises a mixture of oxygenated apatitic calcium phosphate (ApO) of the aforesaid formula and a tricalcium phosphate (PTCa) of the formula $Ca_3(PO_4)_2$.

7. A biomaterial as in claim 1, characterized in that it comprises a mixture of oxygenated apatitic calcium phosphate (ApO) of the aforesaid formula and calcium carbonate $CaCO_3$ and/or calcium sulfate ($CaSO_4$).

8. A biomaterial as in claim 1, characterized in that it comprises a mixture of oxygenated apatitic calcium phosphate (ApO) of the aforesaid formula and a collagen.

9. A biomaterial as in claim 8, characterized in that it comprises a mixture of oxygenated apatitic calcium phosphate (ApO), collagen, glycoaminoglycanes and chondroitine sulfate.

10. A biomaterial as in claim 1 and comprising a mixture of oxygenated apatitic calcium phosphate (ApO) of said formula and one or more compounds selected from fibrin and fibrinogen.

11. A biomaterial as in claim 1, characterized in that it comprises oxygenated calcium phosphate (ApO) with an apatitic structure in which a fraction of the hydrogenophosphate ions ($HPO_4$) is substituted by carbonate ions ($CO_3$).

12. A process for preparation of a biomaterial comprising oxygenated calcium phosphate (ApO) having an apatitic structure having oxygenated species with degrees of oxidation greater than or equal to $-2$, of the formula:

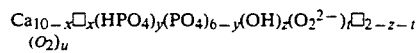

where □ represents a vacancy
$0 \leq x \leq 1$
$0 \leq y \leq 1$
$0 \leq t \leq 1$
$0 \leq u \leq 1$
$u + t \geq 0.2$
and $z = 2 + y - x - 2t$, said process comprising pouring into an aqueous solution containing oxygenated water, a soluble calcium salt and ammonium phosphate, at a pH of 5 to 9, a temperature of 20° C. to 100° C. and for a period of time of from 2 minutes to 300 hours, allowing the precipitate to mature in the mother solution, physically separating the solid phase and the liquid phase and drying said solid phase, and wherein the quantities of calcium salt and of ammonium phosphate salt in the aqueous solution of oxygenated water are such that the Ca/P atomic ratio comprises between 1.4 and 2.

13. A process for preparation as in claim 13 and including adjusting the pH during evolution or during the precipitation to a value between 5 and 9.

14. A process for preparation as in claim 13 and including maintaining the temperature during the evolution or the precipitation at a value between 20° C. and 100° C.

15. A process for preparation as in claim 13 and including fixing the period of time during which the suspension is allowed to develop, or during which the precipitation is carried out, at a value between 2 minutes and 300 hours.

16. A process for preparation as in claim 13 and including providing the aqueous solution containing the oxygenated water with a concentration between 5 and 50 volumes.

17. A process for preparation as in claim 13 characterized in that it comprises a supplementary step of calcining the separated solid phase, at a temperature less than 450°.

18. A process as in claim 12 for preparing a biomaterial having a reduced content of peroxide ions $O^{2-}$, and including after drying, calcining the solid phase at a temperature between 150° and 300°.

19. A process as in claim 12 for preparing a biomaterial
and including preparing said aqueous solution of oxygenated water with a concentration between 25 and 35 volumes,
pouring into said aqueous solution of oxygenated water an aqueous solution of calcium nitrate or calcium acetate and an aqueous solution of ammonium phosphate, in such a manner that the Ca/P atomic ration comprises between 1.3 and 1.7,
mixing the solutions at a pH of between 8 and 9, at a temperature between 75° C. and 100° C. and for a period of time of between 2 and 10 minutes,
separating the solid phase at the end of said period of time and drying the solid phase at a temperature below 100° C.

20. A preparation process as in claim 12 for obtaining a biomaterial comprising mixing the dry solid phase with at least one compound of the following group, present in a finely divided form or in the form of an aqueous gel: HAp, PTCa, $CaCO_3$, $CaSO_4$, collagen, glycoaminoglycane, and chondroitine sulfate.

21. A preparation process as in claim 12 for obtaining a biomaterial comprising adding to the solution containing the oxygenated water, potassium carbonate or sodium carbonate.

* * * * *